United States Patent
Lang

(10) Patent No.: US 8,876,527 B2
(45) Date of Patent: Nov. 4, 2014

(54) ELECTRONIC REGISTER DEVICE FOR RECORDING JAW MOVEMENTS

(75) Inventor: Hans-Walter Lang, Leutkirch (DE)

(73) Assignee: Kaltenbach & Voigt GmbH, Biberach (DE)

(*) Notice: Subject to any disclaimer, the term of this patent is extended or adjusted under 35 U.S.C. 154(b) by 0 days.

(21) Appl. No.: 13/408,100

(22) Filed: Feb. 29, 2012

(65) Prior Publication Data

US 2012/0237892 A1 Sep. 20, 2012

(30) Foreign Application Priority Data

Mar. 18, 2011 (DE) .......................... 10 2011 005 802

(51) Int. Cl.
*A61C 19/04* (2006.01)
*A61C 19/05* (2006.01)
*A61C 19/045* (2006.01)
*A61C 9/00* (2006.01)

(52) U.S. Cl.
CPC ............... *A61C 19/05* (2013.01); *A61C 19/045* (2013.01); *A61C 9/004* (2013.01)
USPC ......................................................... 433/69

(58) Field of Classification Search
CPC ....... A61C 19/045; A61C 19/05; A61C 9/004
USPC .................. 433/68–69, 72–73; 318/568.1, 39
See application file for complete search history.

(56) References Cited

U.S. PATENT DOCUMENTS

| 3,390,459 | A | * | 7/1968 | Murray Seidenberg | ......... 433/27 |
| 4,673,352 | A | * | 6/1987 | Hansen | ........................... 433/69 |
| 7,835,811 | B2 | * | 11/2010 | Schmitt | ........................... 700/98 |
| 2003/0204150 | A1 | * | 10/2003 | Brunner | ........................ 600/590 |
| 2005/0163342 | A1 | * | 7/2005 | Persky | ........................... 382/103 |
| 2007/0190481 | A1 | * | 8/2007 | Schmitt | ........................... 433/68 |
| 2007/0264609 | A1 | * | 11/2007 | Brunner et al. | ................. 433/69 |
| 2009/0068618 | A1 | * | 3/2009 | Lang | ............................ 433/214 |

FOREIGN PATENT DOCUMENTS

WO WO 2007/020091 A1 2/2007
WO WO 2007020091 A1 * 2/2007

* cited by examiner

*Primary Examiner* — Cris L Rodriguez
*Assistant Examiner* — Mirayda A Aponte
(74) *Attorney, Agent, or Firm* — Marshall, Gerstein & Borun LLP

(57) ABSTRACT

An electronic register device for recording movements of the lower jaw of a person relative to the upper jaw of the person, the device having a bite fork for recording a position of the upper jaw relative to reference points on the head of the person, wherein the bite fork is designed to receive a plastic compound for recording an impression of the dentition of the upper jaw.

17 Claims, 9 Drawing Sheets

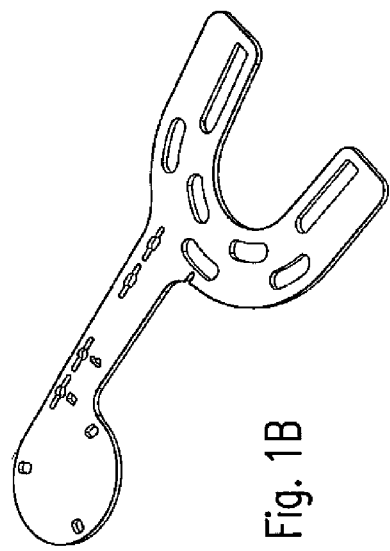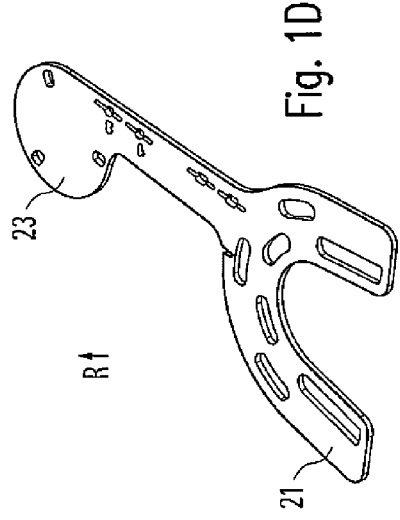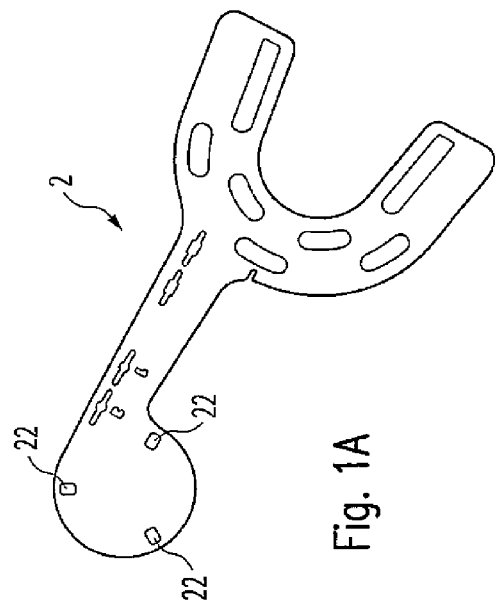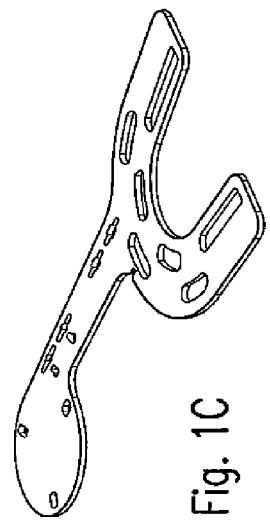
Fig. 1A
Fig. 1B
Fig. 1C
Fig. 1D
Prior art for upper jaw for lower jaw

ELECTRONIC REGISTER DEVICE FOR RECORDING JAW MOVEMENTS

BACKGROUND OF THE INVENTION

1. Field of the Invention

The invention relates to an electronic register device for recording movements of the lower jaw of a person relative to the upper jaw of the person, which register device has a bite fork for recording a position of the upper jaw relative to reference points on the head of the person, wherein the bite fork is designed to receive a plastic compound for recording an impression of the dentition of the upper jaw, and a lower-jaw attachment for recording movements of the lower jaw relative to the upper jaw.

2. Related Technology

To produce tooth replacements such as crowns and bridges, it is known to form models of the dentition of an upper jaw and of the associated lower jaw from wax and to optimize the shape of these models in an articulator, through articulation movements, until a harmonious movement of the tooth shapes in relation to one another is obtained. This is referred to as a functional comparison. In this way, it is subsequently possible to avoid time-consuming grinding work in the mouth of the patient concerned.

According to the prior art, the tooth shape optimized in the articulator is then recorded by scanning and, in a further step, the desired tooth replacement, for example the crown or bridge, is produced, preferably from ceramic, using a CAD CAM milling/grinding machine and the data recorded by the scanning procedure.

A kind of "virtual articulator" is also known. This involves software with which a movement of the two scanned plaster models of the upper jaw and lower jaw relative to each other can be simulated. To be able to determine adjustment data for this virtual articulator, it is first necessary to produce the corresponding plaster models of the dentition of the upper jaw and lower jaw; the adjustment values then have to be determined using these plaster models and a mechanical articulator. This requires quite a lot of work.

WO 2007/020091 A1 discloses an electronic register device which is sold by the applicant under the trade name "ARCUS digma" and which is used to adjust articulators. An electronic analysis of the position of the lower jaw can be performed with this device. In order to measure the movements of the lower jaw relative to the upper jaw, a carrier frame is connected in each case to the upper jaw and the lower jaw. The carrier frame connected on the upper part of the head to the upper jaw, and hereinafter also called the "head part," is provided with four microphones in the form of ultrasound receivers, while the carrier frame connected to the lower jaw, and hereinafter also called the "lower-jaw attachment", is provided with three corresponding ultrasound transmitters. The twelve paths between the three transmitters and the four microphones are evaluated in respect of their changes in length during movements of the lower jaw relative to the upper jaw. FIGS. 2A, 2B, 2C, and 2D show sketches of the lower-jaw attachment from different perspectives.

The head part includes a base element with support elements for supporting the head part on the head of the person concerned or of a patient. These support elements can in particular comprise two rearward bearing elements, which are designed to rest in the area of the two ears, and a nose support, which is designed to rest on the upper nose.

Moreover, the known electronic register device ARCUS digma includes a bite fork, which serves to record the position of the dentition of the upper jaw relative to the auditory canals. FIGS. 1A, 1B, 1C, and 1D show sketches of the bite fork from different perspectives.

SUMMARY OF THE INVENTION

The invention provides a system by which tooth replacements, for example crowns and bridges, can be produced more easily. The invention also permits improved production of drill jigs in implantology.

Accordingly, the invention provides an electronic register device for recording movements of the lower jaw of a person relative to the upper jaw of the person. The register device has a bite fork for recording a position of the upper jaw relative to reference points on the head of the person, wherein the bite fork is designed to receive a plastic compound for recording an impression of the dentition of the upper jaw. Moreover, the register device has a lower-jaw attachment for recording movements of the lower jaw relative to the upper jaw. In addition, the register device has a reference body, wherein the register device is designed so that the reference body can be connected in a fixed position to the bite fork, with the bite fork and the reference body connected thereto in a fixed position being designed in such a way that both the impression and also the reference body can be recorded by a scanning procedure, in particular by a continuous scanning procedure.

By scanning the reference body and the impression, it is possible to maintain or establish a relationship between the scanned impression and the movement data recorded by the register device. In this way, adjustment values for a virtual articulator can be determined without having to produce plaster models of the dentition of the upper and lower jaws.

Moreover, the register device according to the invention allows three-dimensional data of an X-ray system to be superposed with the movement data of the register device. This facilitates the production of drill jigs in implantology.

The reference body preferably has first form-fit elements, and the bite fork has second form-fit elements, such that, in order to produce the positionally fixed connection of the reference body to the bite fork, the first form-fit elements can be brought into a form-fit engagement with the second form-fit elements. The positionally fixed connection between the reference body and the bite fork can thus be produced in a particularly simple and user-friendly manner.

The register device preferably is further designed so that the reference body can also alternatively be connected in a fixed position to the lower-jaw attachment.

The lower-jaw attachment preferably also has third form-fit elements, such that, to produce the positionally fixed connection of the reference body to the lower-jaw attachment, the first form-fit elements can be brought into another form-fit engagement with the third form-fit elements. The positionally fixed connection between the reference body and the lower-jaw attachment can thus be produced in a particularly simple and user-friendly manner.

The reference body advantageously has several, preferably at least three, pin-shaped or hemispherical scan elements, which are preferably designed to protrude from a plane surface of the reference body. At least two of the scan elements preferably have different shapes.

According to another aspect of the invention, an electronic register device is provided for recording movements of the lower jaw of a person relative to the upper jaw of the person, the register device having a bite fork for recording a position of the upper jaw relative to reference points on the head of the person, wherein the bite fork is designed to receive a plastic compound for recording an impression of the dentition of the upper jaw. Moreover, the register device has a lower-jaw attachment for recording movements of the lower jaw relative to the upper jaw. The bite fork has a first reference body, which is connected in a fixed position to the rest of the bite fork, and the lower-jaw attachment has a second reference body, which is connected in a fixed position to the rest of the lower-jaw attachment. The bite fork is designed in such a way that both the impression and also the first reference body can be recorded by a scanning procedure, in particular a continuous scanning procedure.

The first reference body and the second reference body preferably each have several, highly preferably in each case at least three, pin-shaped or hemispherical scan elements, which are each preferably designed to protrude from a plane surface of the reference body in question.

Moreover, at least two of the scan elements of the first reference body preferably have different shapes, and/or at least two of the scan elements of the second reference body have different shapes.

BRIEF DESCRIPTION OF THE DRAWINGS

The invention is explained in more detail below on the basis of illustrative embodiments and with reference to the drawings, in which:

FIGS. 1A to 1D show sketches of a bite fork from different perspectives,

DETAILED DESCRIPTION

Figure 2A:
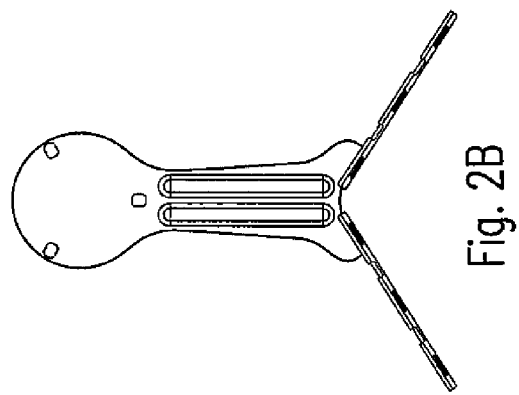
FIGS. 2A to 2D show sketches of a lower-jaw attachment from different perspectives.
Figure 2C:
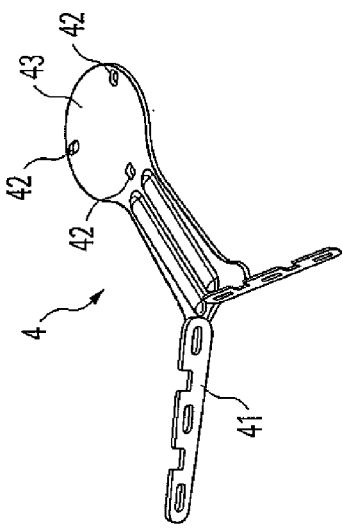
Figure 2B:
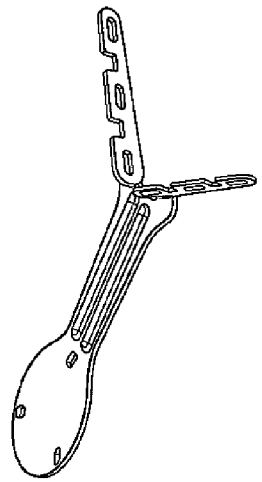
Figure 2D:
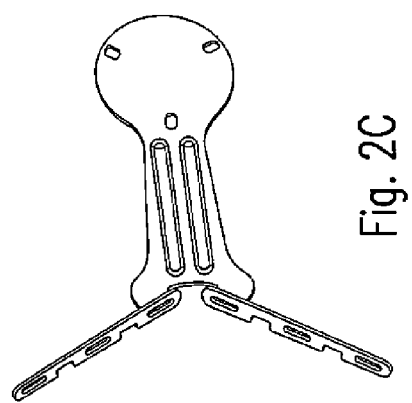

According to the invention, an electronic register device is provided for recording movements of the lower jaw of a person relative to the upper jaw of the person. The register device can have the features of the "ARCUS digma" device mentioned in the introduction. In particular, the register device can include a corresponding head part, which includes a base element with support elements for supporting the head part on the head of a patient. These support elements can in particular include two rearward bearing elements, which are designed to rest in the area of the two ears, for example to rest in the external auditory canals, and also a nose support, which is designed to rest on the upper nose.

The register device furthermore includes a bite fork, which is designed and used to record a position of the upper jaw relative to reference points on the head of the person. As has already been mentioned in the introduction, FIGS. 1A to 1D show sketches of a known design of a bite fork 2 from different perspectives. The bite fork 2 is designed to receive a plastic compound, for example wax or silicone, for recording an impression of the dentition of the upper jaw. For this purpose, the bite fork 2 has a receiving surface 21 for receiving the plastic compound, wherein the receiving surface 21 has a surface normal in a direction R; moreover, the bite fork 2 has another surface 23, the surface normal of which likewise points in the direction R, wherein the bite fork 2 is designed in such a way that the other surface 23 is located outside the oral cavity of the person when the bite fork 2 is positioned for taking the impression of the dentition of the upper jaw.

The register device further includes a lower-jaw attachment. As has already been mentioned in the introduction, FIGS. 2A to 2D show sketches of a known lower-jaw attachment 4 from different perspectives. The lower-jaw attachment 4 serves for recording movements of the lower jaw relative to the upper jaw. The lower-jaw attachment has an angled, elongate contact area 41, which is intended to be connected, for example by an adhesive connection, to the anterior surfaces of the front teeth of the lower jaw. Moreover, the lower-jaw attachment has a surface 43, which is oriented at least approximately in a plane fixed by the elongate contact area 41 and which is located outside the oral cavity of the person when the lower-jaw attachment 4 is connected as intended to the teeth of the lower jaw.

Figure 3A:
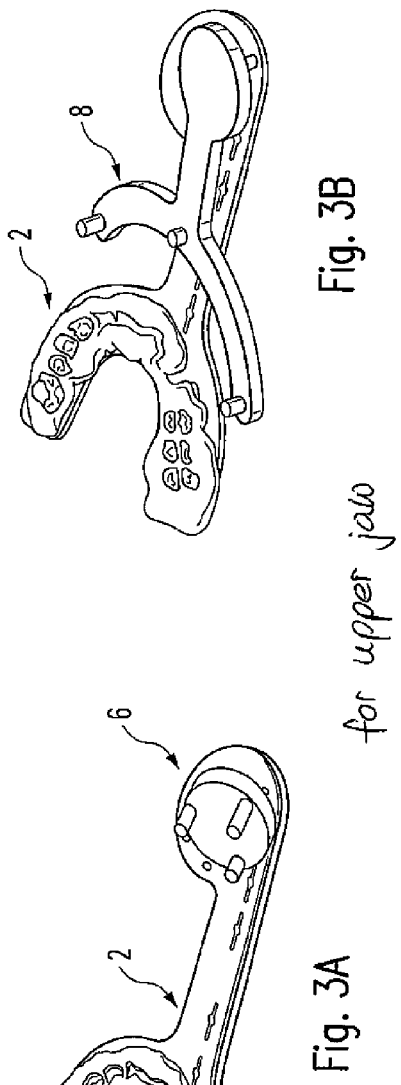
FIG. 3A shows a bite fork with a first illustrative embodiment of a reference body according to the invention.
Figure 4:
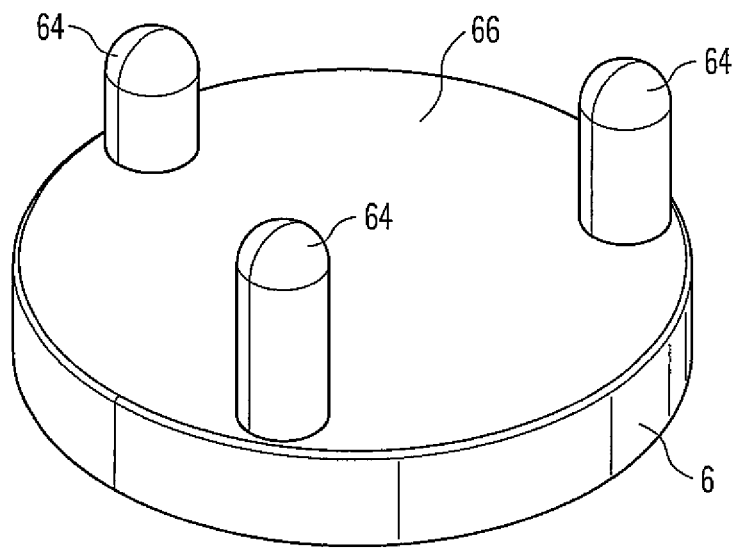
FIG. 4 shows a perspective view of the reference body according to the first illustrative embodiment.

The register device, in contrast to the "ARCUS digma" device, also has a reference body. FIG. 4 shows a reference body 6 according to a first illustrative embodiment. The register device is designed in such a way that the reference body 6 can be connected in a fixed position, and preferably reversibly in a fixed position, to the bite fork 2, as indicated in FIG. 3A. In other words, the design is such that the reference body 6 can be connected to the bite fork 2 in a defined position relative to the latter.

Figure 6A:
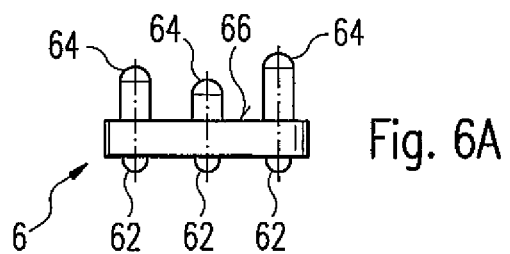
FIGS. 6A to 6C show further sketches of the reference body according to the first illustrative embodiment.
Figure 6B:
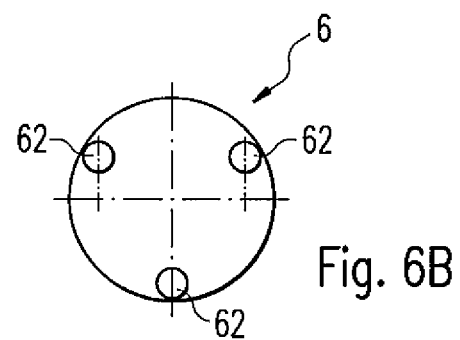
Figure 6C:
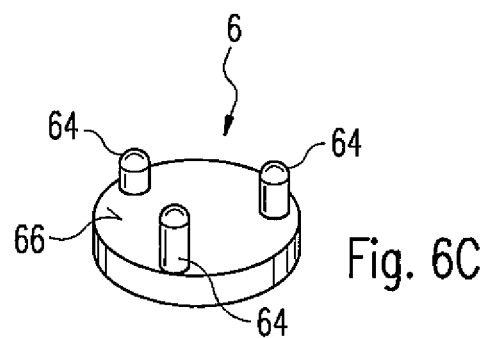

In particular, a form-fit engagement can be provided for this purpose between the reference body 6 and the bite fork 2. This permits particularly simple handling. For this purpose, as is indicated by way of example in FIG. 6A, the reference body 6 can have first form-fit elements 62 and, as is indicated by way of example in FIG. 1A, the bite fork 2 can have second form-fit elements 22 which, in order to produce the form-fit engagement, can be connected in a defined manner to the first form-fit elements 62. The first form-fit elements 22 can be formed by at least three engagement elements, and the second form-fit elements 22 can be formed by correspondingly shaped and congruent openings. This permits particularly simple handling when producing the positionally fixed connection of the reference body 6 to the bite fork 2. FIGS. 6B and 6C show sketches of the reference body 4 from other perspectives.

Moreover, FIG. 3A indicates a corresponding impression 10 of the dentition of the upper jaw.

Provision is preferably made that the reference body 6, in order to produce the positionally fixed connection, can be arranged on the other surface 23 of the bite fork 2. For this purpose, the second form-fit elements 22 or the openings can be formed on or in the other surface 23 of the bite fork 2.

Figure 8:
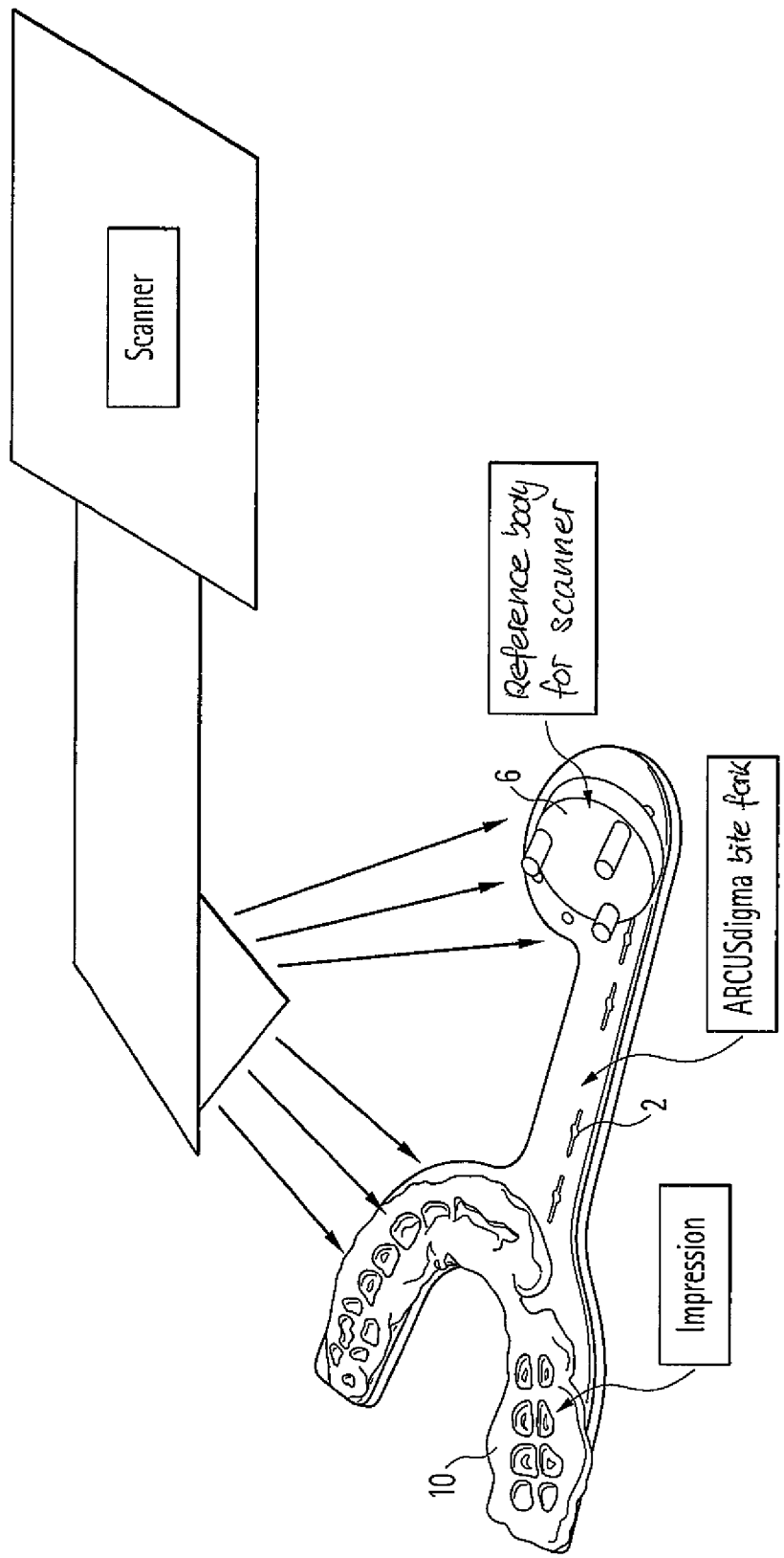
FIG. 8 shows a block diagram illustrating the use of a bite fork with the reference body according to the first illustrative embodiment.

The register device is designed in such a way that both the impression 10 of the dentition of the upper jaw, recorded with the bite fork 2, and also the reference body 6 can be recorded by a scanning procedure, in particular by a scanning procedure in which the position of the reference body 6 relative to the impression 10 can be recorded. This is indicated diagrammatically in FIG. 8. Such a scanning procedure allows a relationship to be established between, on the one hand, the scanned impression 10 and, on the other hand, the movement data recorded by the register device. In this way, adjustment values for a virtual articulator can be determined, in particular without having to produce plaster models of the dentition of the upper jaw and lower jaw. Moreover, the register device according to the invention allows three-dimensional data of an X-ray system to be superposed with the movement data of the register device. This facilitates production of drill jigs in implantology. For the assignment of the two systems ARCUS digma and CAD CAM or ARCUS digma and 3D scan, the entire structural component consisting of the bite fork 2 and of the reference body 6 is scanned. The tooth impressions and on the teeth are recorded in relation to the scanner or reference body 6 in one scan.

Figure 3B:
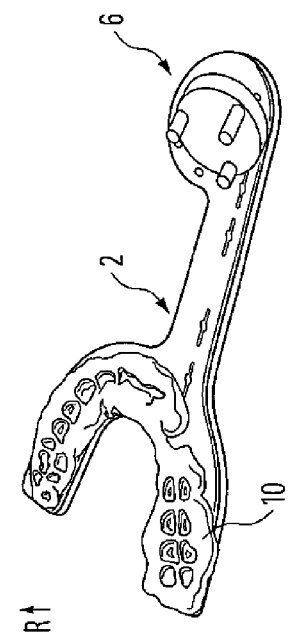
FIG. 3B shows a bite fork with a second illustrative embodiment of a reference body according to the invention.
Figure 3D:
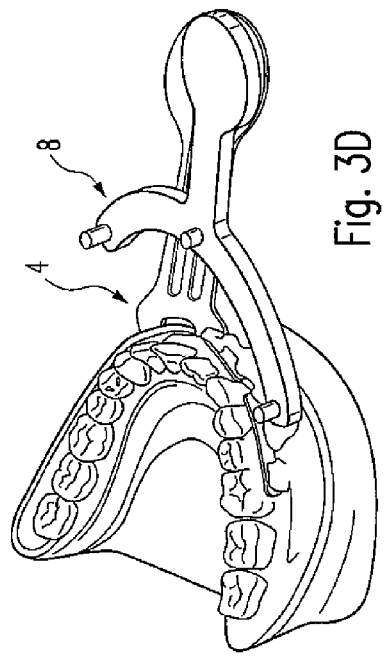
FIG. 3D shows a lower-jaw attachment with a reference body according to the second illustrative embodiment.
Figure 3C:
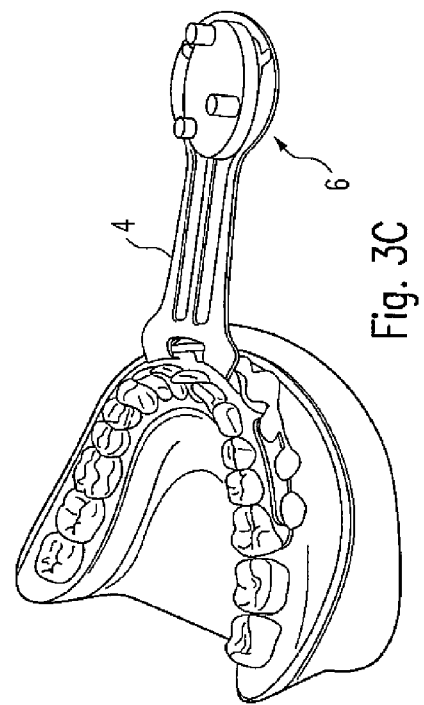
FIG. 3C shows a lower-jaw attachment with a reference body according to the first illustrative embodiment.

The register device is preferably also designed in such a way that the reference body 6 can also be connected in a fixed position to the lower-jaw attachment 4, as is indicated by way of example in FIG. 3C. For this purpose, the lower-jaw attachment 4 can advantageously have third form-fit elements 42, particularly in the form of openings, which are shown by way of example in FIG. 2A and which are preferably shaped analogously to the second form-fit elements 22 or the openings of the bite fork 2. In this way, the reference body 6 can be mounted particularly easily either on the bite fork 2 or on the lower-jaw attachment 4. The third form-fit elements 42 are advantageously formed on or at the surface 43 of the lower-jaw attachment 4.

The reference body 6 advantageously has several, preferably at least three, pin-shaped or hemispherical scan elements 64, which are preferably designed to protrude from a plane surface 66 of the reference body 6. The configuration is preferably such that the scan elements 64 are arranged or designed to protrude in direction R from the rest of the reference body 6 or the plane surface 66 when the reference body 6 is connected in a fixed position to the bite fork 2. At least two of the scan elements 64 advantageously have different shapes. For instance, as is indicated by way of example in FIGS. 4, 6A, and 6C, pins of different lengths can be provided as scan elements 64.

Figure 5:
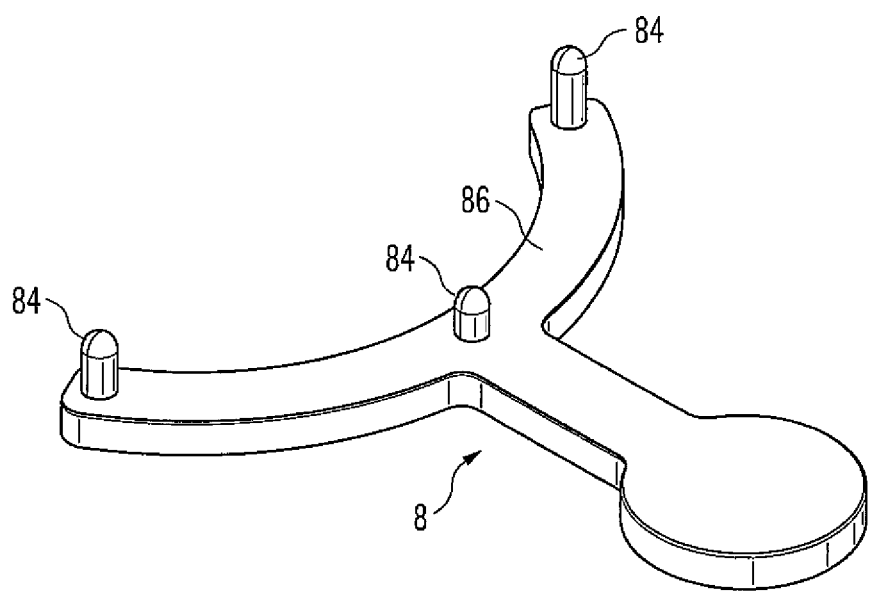
FIG. 5 shows a perspective view of the reference body according to the second illustrative embodiment.
Figure 7A:
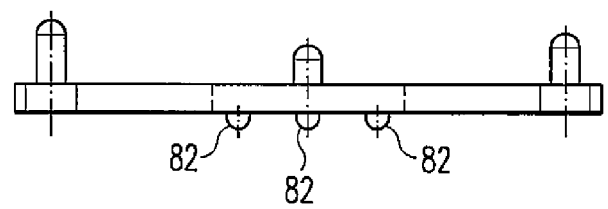
FIGS. 7A to 7C show further sketches of the reference body according to the second illustrative embodiment.
Figure 7B:
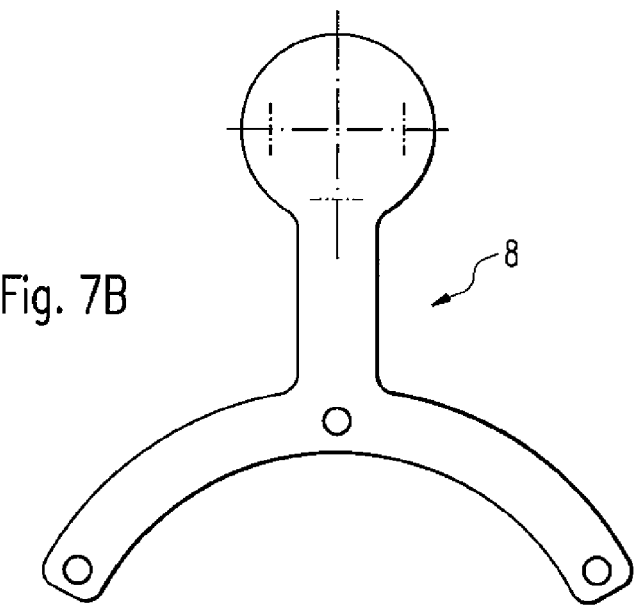
Figure 7C:
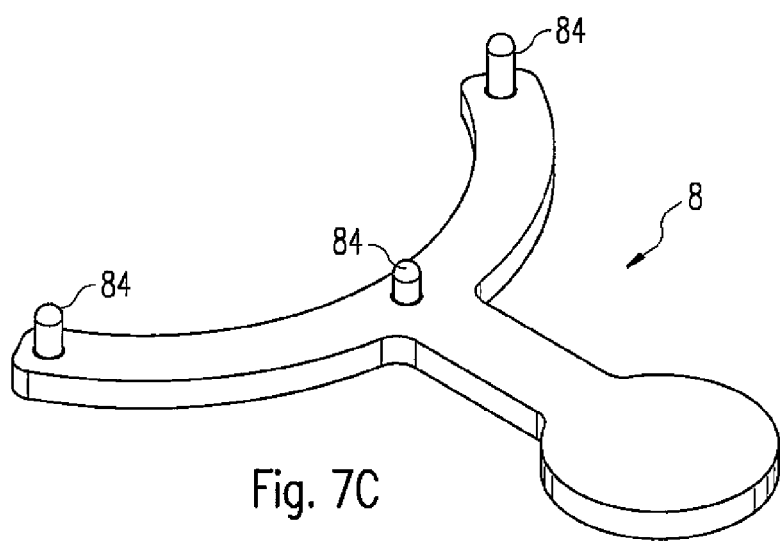

FIG. 5 shows a reference body 8 according to a second illustrative embodiment. This reference body 8 can have scan elements 84, which are designed analogously to the scan elements 64 in the first illustrative embodiment. Moreover, the reference body 8 according to the second illustrative embodiment can have corresponding first form-fit elements 82 or engagement elements, as are indicated in FIG. 7A. The reference body 8 according to the second illustrative embodiment is shown in FIG. 3B connected to the bite fork 2 and in FIG. 3D connected to the lower-jaw attachment 4. FIGS. 7B and 7C show other views of the reference body 8 according to the second illustrative embodiment.

Figure 9:
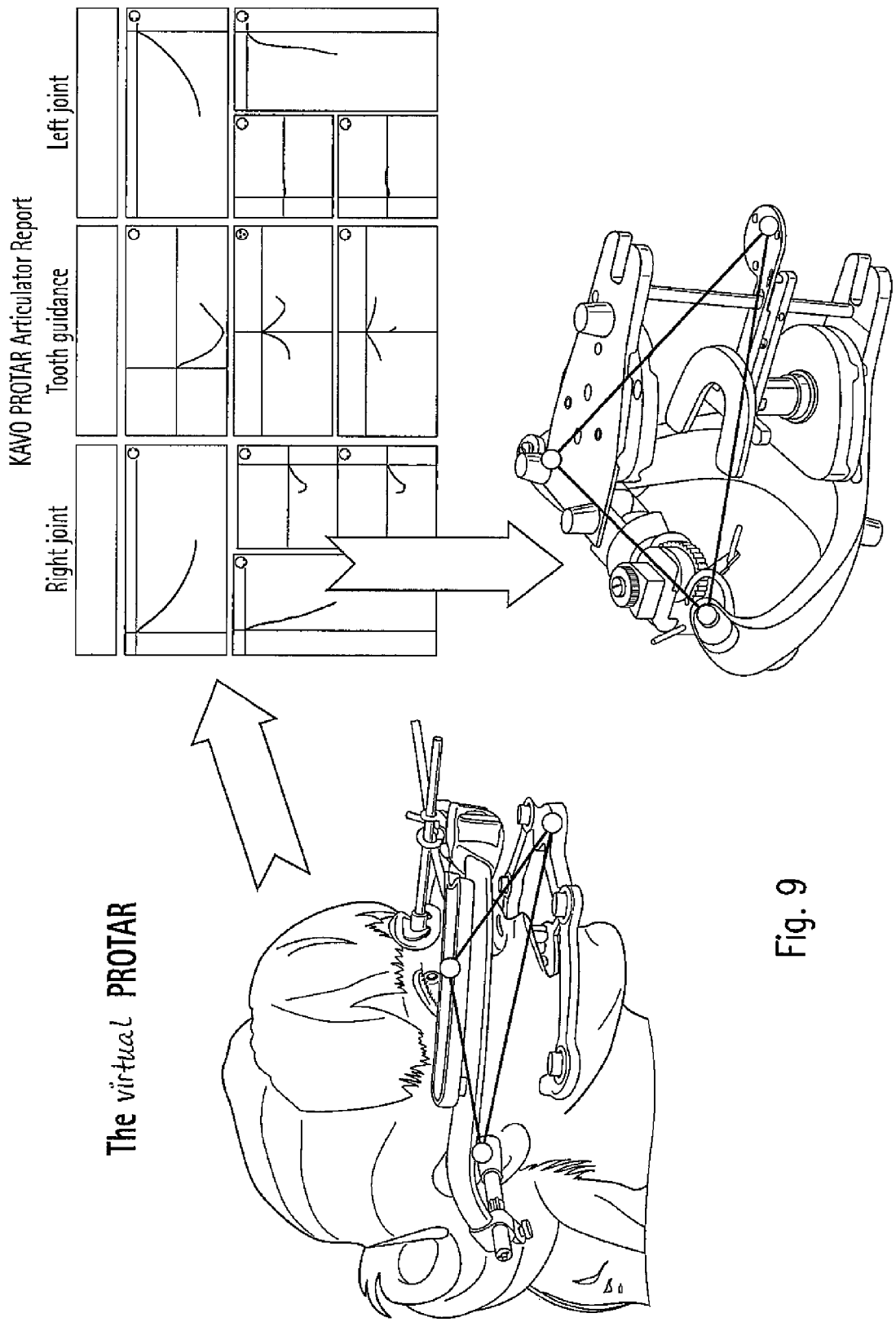
FIG. 9 shows a sketch illustrating reference points between an "ARCUS digma" and an articulator.
Figure 10:
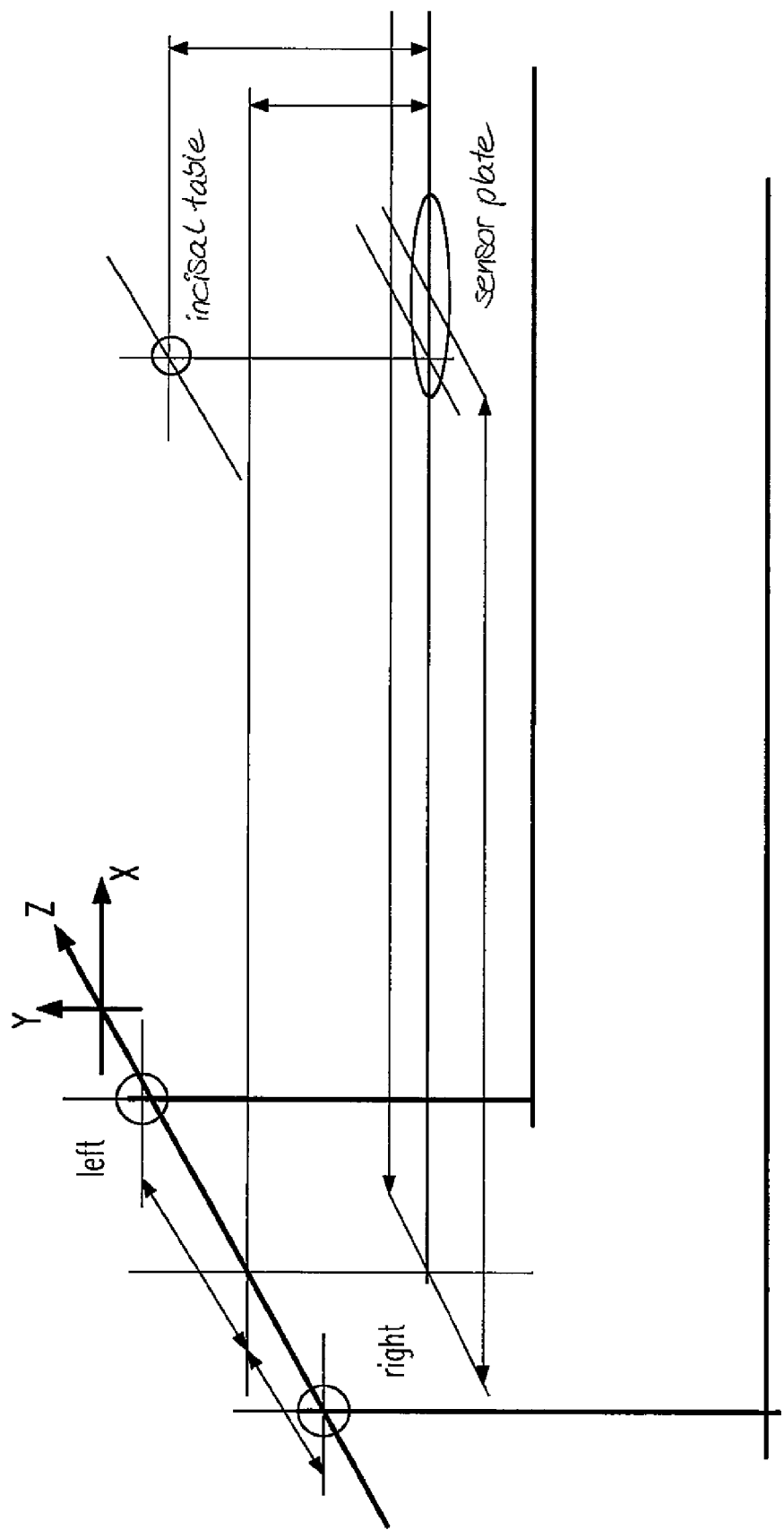
FIG. 10 shows a sketch illustrating reference points of an articulator.

FIG. 9 shows an assignment of reference points between the electronic register device and an articulator. A corresponding system of coordinates is shown in sketch form in FIG. 10.

As an alternative to the above-described reference body 6 or 8, provision can be made that the bite fork of the electronic register device has a first reference body, which is connected in a fixed position to the rest of the bite fork, and that the lower-jaw attachment has a second reference body, which is connected in a fixed position to the rest of the lower-jaw attachment, wherein the bite fork is designed in such a way that both the impression and also the first reference body can be recorded by a corresponding scanning procedure. The first reference body can advantageously be formed integrally with the rest of the bite fork, and the second reference body can be formed integrally with the lower-jaw attachment. The two reference bodies preferably each have scan elements, which are designed analogously to the above-described scan elements 64 of the reference body 6 according to the first illustrative embodiment.

The invention claimed is:

1. Electronic register device for recording movements of the lower jaw of a person relative to the upper jaw of the person, the register device comprising:
    a bite fork for recording a position of the upper jaw relative to reference points on the head of the person, wherein the bite fork is designed to receive a plastic compound for recording an impression of the dentition of the upper jaw,
    a lower-jaw attachment for recording movements of the lower jaw relative to the upper jaw, and
    a reference body,
    wherein the reference body is adapted to be connected in a fixed position to the bite fork, wherein the bite fork and the reference body connected to it in a fixed position are designed such that both the impression and the reference body are arranged to be recorded by a scanning procedure, the reference body including a plurality of scan elements, and the scan elements protruding from a plane surface of the reference body in a direction opposite to a form-fit-element.

2. Electronic register device of claim 1, wherein the impression and the reference body are recorded together by a continuous scanning procedure.

3. Electronic register device of claim 1, wherein the reference body is adapted to be alternatively connected in a fixed position to the lower-jaw attachment.

4. Electronic register device of claim 1, wherein the reference body has a plurality of first form-fit elements, and the bite fork has a plurality of second form-fit elements, such that, to produce the positionally fixed connection of the reference body to the bite fork, the first form-fit elements are adapted to be brought into a form-fit engagement with the second form-fit elements.

5. Electronic register device of claim 4, wherein the reference body is arranged to be alternatively connected in a fixed position to the lower-jaw attachment.

6. Electronic register device of claim 5, in which the lower-jaw attachment has a plurality of third form-fit elements, such that, to produce the positionally fixed connection of the reference body to the lower-jaw attachment, the plurality of first form-fit elements is adapted to be brought into form-fit engagement with the plurality of third form-fit elements.

7. Electronic register device of claim 6, wherein the third form-fit elements are openings.

8. Electronic register device of claim 7, wherein one of the third form-fit elements is shaped analogously to the at least one first form-fit element.

9. Electronic register device of claim 4, wherein one of the plurality of the second form-fit elements is an opening.

10. Electronic register device of claim 1, wherein the reference body has at least three said scan elements.

11. Electronic register device of claim 1, wherein the reference body is removable from the bite fork.

12. Electronic register device for recording movements of the lower jaw of a person relative to the upper jaw of the person, the register device comprising:
    a bite fork for recording a position of the upper jaw relative to reference points on the head of the person, wherein the bite fork is designed to receive a plastic compound for recording an impression of the dentition of the upper jaw, and a lower-jaw attachment for recording movements of the lower jaw relative to the upper jaw, wherein the bite fork has a first reference body connected in a fixed position to the rest of the bite fork, and the lower-jaw attachment has a second reference body connected in a fixed position to the rest of the lower-jaw attachment, wherein the bite fork is designed in such a way that both the impression and also the first reference body can be recorded by a scanning procedure, wherein one of the first reference body and the second reference body includes a plurality of scan elements that protrude from a plane surface of the at least one of the first reference body and the second reference body in a direction opposite to a form-fit element.

13. Electronic register device of claim 12, wherein the scanning procedure is a continuous scanning procedure.

14. Electronic register device of claim 12, wherein the first reference body and the second reference body each have several pin-shaped or hemispherical scan elements.

15. Electronic register device of claim 13, wherein one of the first reference body and the second reference body has at least three said scan elements.

16. Electronic register device of claim 12, wherein the first reference body is removable from the bite fork.

17. Electronic register device of claim 12, wherein the second reference body is removable from the lower-jaw attachment.

* * * * *